United States Patent
Sundermann et al.

(10) Patent No.: US 7,021,118 B2
(45) Date of Patent: Apr. 4, 2006

(54) METHOD OF TESTING A RADIOLOGY APPARATUS AND COMPUTER PROGRAM

(75) Inventors: Dietmar Sundermann, Orsay (FR); Lionel Desponds, St Remy-les-Chevreuse (FR); Jean-Luc Duflot, Maurepas (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/867,536

(22) Filed: Jun. 14, 2004

(65) Prior Publication Data

US 2004/0223591 A1 Nov. 11, 2004

Related U.S. Application Data

(62) Division of application No. 09/879,488, filed on Jun. 12, 2001, now Pat. No. 6,850,596.

(30) Foreign Application Priority Data

Jun. 16, 2000 (FR) .................................. 00 07745

(51) Int. Cl.
*G21K 1/02* (2006.01)

(52) U.S. Cl. ...................................... 73/1.79; 378/207

(58) Field of Classification Search ................. 73/1.01, 73/1.75, 1.79, 865.9; 378/145, 146, 156, 378/157, 160, 161, 204, 205, 206, 207, 208
See application file for complete search history.

(56) References Cited

U.S. PATENT DOCUMENTS

| 4,023,036 A | | 5/1977 | Barrett et al. | |
|---|---|---|---|---|
| 4,246,488 A | | 1/1981 | Hura | |
| 5,056,130 A | | 10/1991 | Engel | |
| 5,394,455 A | * | 2/1995 | Roeck et al. | 378/98.3 |
| 5,625,661 A | | 4/1997 | Oikawa | |
| 5,841,835 A | | 11/1998 | Aufrichtig et al. | |
| 6,285,902 B1 | * | 9/2001 | Kienzle et al. | 600/427 |
| 6,697,664 B1 | * | 2/2004 | Kienzle, III et al. | 600/427 |
| 2001/0001107 A1 | * | 5/2001 | Weinberg | 600/425 |
| 2003/0038240 A1 | * | 2/2003 | Weinberg | 250/363.02 |

FOREIGN PATENT DOCUMENTS

| DE | 197 07 728 A1 | 8/1998 |
|---|---|---|
| EP | 0 874 536 A1 | 10/1998 |
| FR | 2 700 909 A1 | 7/1994 |
| FR | 2 601 544 A1 | 1/1998 |

OTHER PUBLICATIONS

Chu, Robert Y.L. et al. "Standardized Methods for Measuring Diagnostic X-Ray Exposures". *Report of Task Group 8, Diagnostic X-Ray Imaging Committee*. AAPM Report No. 31. Jul. 1990.

(Continued)

*Primary Examiner*—Eric S. McCall
(74) *Attorney, Agent, or Firm*—Cantor Colburn LLP

(57) ABSTRACT

Collimation device of the type intended to direct an energy beam in a given direction and at a given solid angle, the collimation device being capable of being installed on output of an energy beam generating arrangement and of being connected to a control unit. The collimation device includes the ability for testing operation of the assembly formed by the energy beam generating arrangement, the collimation device and the control unit.

9 Claims, 6 Drawing Sheets

OTHER PUBLICATIONS

Sieband, M. et al. "Basic Quality Control in Diagnostic Radiology". *Diagnostic Radiology Control Task Force of Quality Assurance Protocol.* AAPM Report No. 4. Nov. 1977.

Wagner, Louis K. et al. "On the Measurement of Half-Value Layer in Film-Screen Mammography". *Med. Phy. 17(6)*, Nov./Dec. 1990. AAPM 0094-2408/90/060989-09. 1990.

Waggener, Robert G. et al. "X-Ray Spectra Estimation Using Attenuation Measurements from 25kVp to 18MV". *Med. Phy. 26(7)*, Jul. 1999. AAPM 0094-2405/99/26(7)/1269/10. 1999.

Rossi, Raymond P. et al. "Performance Specification and Acceptance Testing for X-Ray Generators and Automatic Exposure Control Devices". *Report of the Diagnostic X-Ray Imaging Committee Task Group on Performance Specifications and Acceptance Testing for X-ray Generators and Automatic Exposure Control Devices.* AAPM Report No. 14. Jan. 1985.

High, Maynard et al. "Performance Evaluation and Quality Assurance in Digital Substraction Angiography". *A Report of the Digital Radiography/Flourography Task Group Diagnostic X-Ray Imaging Committee American Association of Physicists in Medicine.* AAPM Report No. 15. May. 1985.

\* cited by examiner

METHOD OF TESTING A RADIOLOGY APPARATUS AND COMPUTER PROGRAM

CROSS REFERENCE TO RELATED APPLICATIONS

This application claims the benefit of a priority under 35 USC 119 to French Patent Application No. 0007745 filed Jun. 16, 2000, the entire contents of which are incorporated by reference. This application is a divisional application of U.S. application Ser. No. 09/879,488 filed Jun. 12, 2001 now U.S. Pat. No. 6,850,596.

BACKGROUND OF THE INVENTION

The present invention concerns the field of electromagnetic radiation beams used for different types of measurement and visualization. The invention is applicable notably to X-ray imaging or processing devices, for example, in the medical field.

A radiology apparatus generally comprises means for an X-ray emission having equipped with an X-ray tube and a collimator, means for receiving the X-ray emissions separated from the means for emission by a distance sufficient to place there an object that it is desired to study. The collimator serves to determine the solid angle of aperture of the X-ray beam. The X-ray beam can thus be limited to the surface of the receiver. The collimator can also serve to further reduce the solid angle of the beam in order to limit it to a particular zone of interest of the object that is studied or processed, which makes it possible to prevent other parts of the object from being subjected to X-rays. The collimator can include a diaphragm made according to the principle of the diaphragm of a camera of articulated moving plane type. A diaphragm whose attenuating material consists of a deformable solid or of a fluid in a chamber is also disclosed in FR-A-2,601,544.

In addition, a radiology apparatus further comprises an electronic control unit for the X-ray tube, collimator, receiver (provided, for example, with a scintillator), a high-voltage supply of the X-ray tube, etc.

Such an apparatus must be calibrated in order to attain a sufficient qualitative and quantitative precision of the structures observed on an image. The calibration is generally done by means of a phantom that is placed at the object site on the path of the X-ray beam. A phantom is an object separate from the apparatus and comprising parts opaque to X-rays arranged according to a geometry defined and known. An image of the phantom is acquired under the geometric conditions of an angle of incidence that it is sought to be calibrated. The projections of the characteristic points are then recognized in the image. Each characteristic point of the object is associated with its trace in the acquired image. The system of equation describing the projection supplying the image is inverted in the mathematical sense and the set of parameters of the projection is finally obtained for the given vantage point. A phantom and method of calibration of an X-ray imaging system is disclosed in FR-A-2,700,909 and EP-A-0,874,536.

BRIEF DESCRIPTION OF THE INVENTION

An embodiment of the present invention is directed to increasing the automation of calibration of a system using electromagnetic radiation. An embodiment of the present invention proposes controlling the calibration. An embodiment of the present invention proposes a phantom whose risks of deterioration are reduced.

A collimation device, according to one embodiment of the invention, is of the type intended to direct an energy beam in a given direction and at a given solid angle. The collimation device is capable of being installed on output of an energy beam generating means and of being connected to the control unit. The collimation device includes means for testing operation of the assembly formed by the energy beam generating means, the collimation device, the control device and a receiver. The means can be integrated with the device, for example, by being adjacent to the collimation elements. The means can be connected to the control unit directly or indirectly. The collimation device advantageously includes means for calibrating the operating parameters intended to be used by the control unit. In an embodiment of the invention, the collimation device includes means for testing the operation of an X-ray tube emitting the energy beam. The means are preferably capable of being commanded by a control unit. In an embodiment of the invention, the means are capable of being remote-controlled by a computer installed on another site.

In an embodiment of the invention, the means include a plurality of test tools with a position sensor of each tool. The collimation device can include a motion sensor of each tool. The progress or temporal change of the calibration can then be monitored.

A radiology apparatus, according to one aspect of the invention, means for emitting an energy beam means of reception for the energy beam, a control unit and a collimation device, such as described above.

A test kit, according to one embodiment of the invention, includes means for fastening to a collimation device, of the type designed to direct an energy beam in a given direction and at a given solid angle and means for testing the operation of the collimation device means for emitting energy beam and a control unit. The test kit can advantageously be equipped with means for communicating with the control unit. The test kit is therefore capable of being fastened to collimation device, notably, below the latter in the direction of propagation of the energy beam. The test kit can be fastened on a collimation device with little or no structural modifications.

The invention also proposes a method for testing a radiology apparatus, in which the operation of the apparatus is tested by means of tools forming part of a collimation device, the tools making it possible to functionally define the operation of the means for emitting an energy beam of the collimation device and of a receiver.

The invention is also directed to a computer program including means for providing a program code for applying the steps of the above-mentioned method.

The invention likewise is directed to a storage medium capable of being read by a device for reading the program code which are stored there in and which are capable of applying the steps of the abovementioned method.

The invention also makes possible a remote control of the quality of operation of an apparatus, notably of a radiology apparatus, by making possible a calibration remote-controlled from a maintenance center, for example, with telecommunication through an Internet-type network, or an automatic calibration at given time intervals or operating times, while providing for the possibility that a negative result of automatic calibration might trip an alarm in a maintenance center which can also be remotely situated.

For that purpose, the collimation device may comprise: one or more lead plates for calibration of the X-ray tube that is done by emitting X-rays; one or more copper plates for calibration of the gain response of the entire information processing system formed by the apparatus, which makes it possible to characterize, notably, the aging of the X-ray tube; one or more aluminum plates for spectral characterization of the X-ray beam and dose measurement. Several aluminum plates will preferably be provided to determine at what thickness of aluminum the dose is divided by a given factor; one or more wires of radiation-absorbent material; one or more grids of radiation-absorbent material; one or more plates of radiation-absorbent material of thickness calibrated in steps to make calibration of the image quality possible.

The persistence or kinetic blur due, for example, to the scintillator, which continues to emit an output signal when the input signal (X-rays) has been interrupted can be calibrated. The progress of presistence is monitored by placing one or more test objects in the beam, automatically controlling the speed and position of the test objects.

BRIEF DESCRIPTION OF THE DRAWINGS

An embodiment of the invention is illustrated by the attached drawings in which.

DETAILED DESCRIPTION OF THE INVENTION

Figure 1:
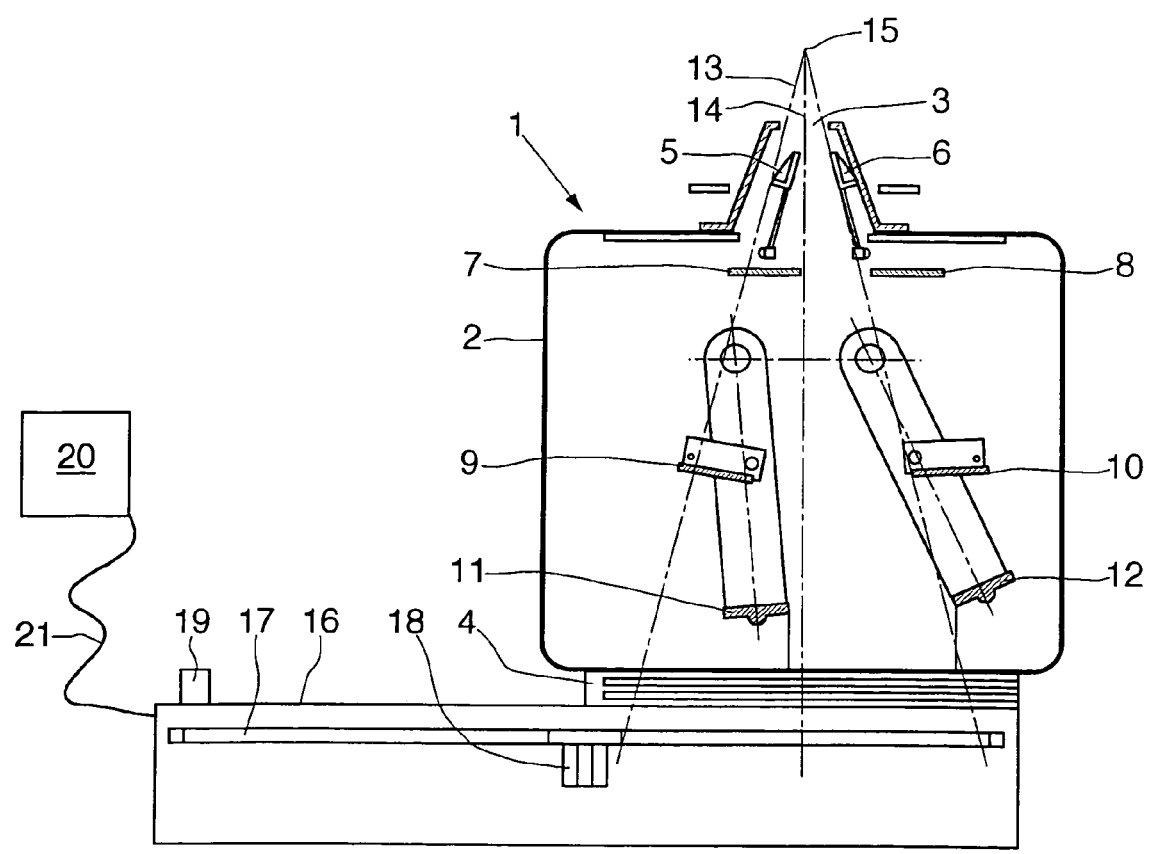
FIG. 1 is a schematic view of a collimator.

In FIG. 1, a collimation device 1 comprises a casing 2 provided with an inlet 3, an outlet 4 and a plurality of moving plates 5 to 12 opaque to X-rays. Plates 5 to 12 provide a collimation according to a rectangular format of an X-ray beam 13 represented by a line of dots and dashes being propagated on an axis 14. The beam emanates from a focus 15 situated in an X-ray tube not represented. Collimation makes it possible to adapt the beam to the shapes of rectangular detectors of film, scintillator and CCD camera type, or solid state detectors, or organs crossed by the X-ray beam.

The collimation device 1 also includes an additional casing 16 placed in contact with the lower aperture 4 of casing 2 and also arranged to be transparent to X-rays. Inside casing 16, there is a disk 17 rotary-mounted and driven by a motor 18, the rotation being detected by a sensor 19, for example, of optical type reading an optical coder, not represented, which can comprise a sequence of alternate light and dark zones arranged on the upper surface of the disk 17, close to its periphery, opposite the sensor 19.

Figure 2:
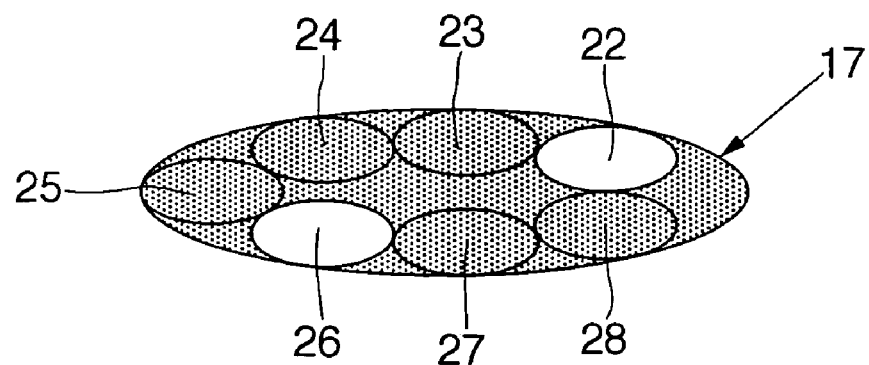
FIGS. 2, 4, 6 and 7 are schematic views in perspective of test tools.

An embodiment of the disk 17 is illustrated in FIG. 2. The disk 17 comprises a plurality, for example seven, of circular zones 22 to 28. The diameter and the positioning of the circular zones 22 to 28 on the disk 17 are such that the X-ray beam 13 illustrated in FIG. 1 presents a diameter slightly less than that of one of the circular zones 22 to 28, when it crosses one of the circular zones 22 to 28. Circular zone 22 is empty and is used in normal operation of a radiology apparatus, for example, on taking an X-ray image of a patient. Circular zone 23 is an aluminum plate of given thickness that allows testing of the variation of spectral quality due to aging of the X-ray tube, which makes it possible to determine when it is advisable to change the tube in order to avoid a shutdown of the radiology apparatus due to a malfunction. The information on change of spectral quality can also be used for calibration of the exposure parameters, such as high service voltage of the X-ray tube, service current, etc. Circular zone 24 comprises a two-dimensional phantom such as a metal grid of given material and thickness. Circular zone 25 also comprises a phantom, for example, in the form of a sheet with defined beveled edges. Those two phantoms make possible an evaluation of image quality. Circular zone 26 comprises a plate of heavy metal, for example, 2 mm thickness of lead, which makes it possible to totally block the X-ray beam. Circular zone 27 comprises a copper plate of given thickness, for example, 2 mm. Circular zone 28 also comprises a copper plate of different thickness from circular zone 27. Both circular zones 27 and 28 can be used for calibration of the X-ray dose without it being necessary to use a dosimeter.

A motor 18 for turning the disk 17 on instruction of the radiology apparatus control unit 20, allows the different steps of calibration to proceed automatically. The intervention of an operator can be reduced to the decision to initiate calibration. The operator can be located on site or at a remote maintenance center connected by digital link to the radiology apparatus. Calibration can also be carried out automatically, for example, outside of normal working hours of the radiology apparatus and the necessary adjustments of the parameters of the radiology apparatus can be made while being able to signal a fault requiring attention by means of a local alarm and/or to a remote maintenance center. A sensor 19, makes it possible to ascertain the position and possibly the speed of rotation of the disk 17, is also connected to the control unit 20 of the radiology apparatus.

As can be seen in FIG. 1, the control unit 20 is joined by a wire connection 21 to the operation test means formed by the casing 16 equipped with the disk 17, motor 18 and sensor 19. However, a wireless link or even a connection through casing 2 could also be provided. The control unit 20 can be dedicated to the operation test means, or dedicated to the collimation device 1, or can form a central control unit of the radiology apparatus to which the collimation device 1 is a part. The control unit 20 includes at least one processor, at least one memory and at least one set of control instructions stored in memory and capable of being executed by the processor.

Figure 3:
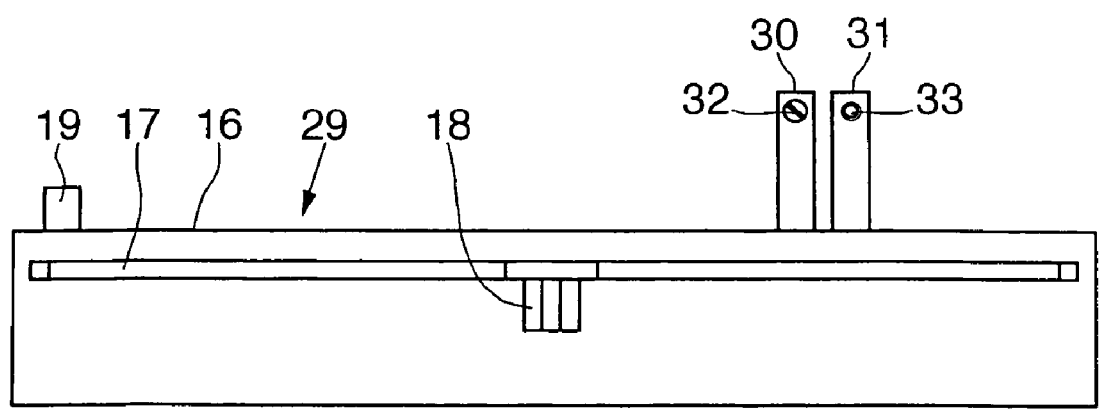
FIG. 3 is a schematic view of a test kit.

Casing 16 and casing 2 can be interlocked, for example, by means of screws, not represented. Casings 2 and 16 can also be made in a single unit. If casing 16 is separate from casing 2, it can be arranged to add an operation test means to the collimation device in the existing radiology apparatus, as shown in FIG. 3. In the latter case, the test means may be in the form of a test kit 29 having a general shape similar to the test means of the embodiment of FIG. 1 and provided, in addition, with two lugs 30 and 31, each provided with a screw 32, 33 capable of cooperating in corresponding tapped holes of a collimation device casing.

Figure 4:
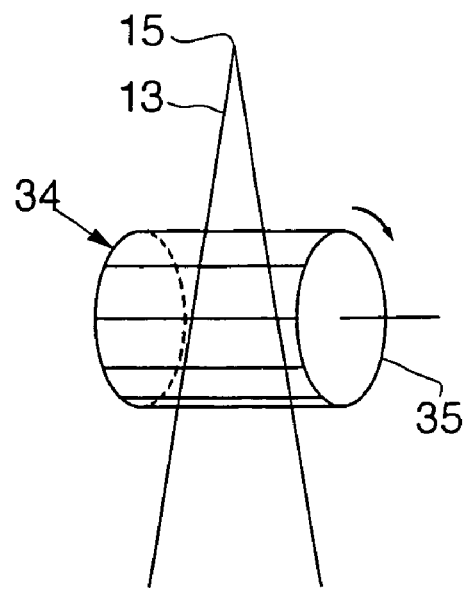
Figure 5:
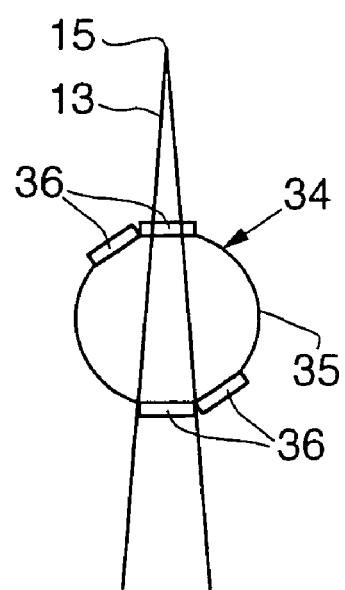
FIG. 5 is a schematic side view in elevation of the test tool of FIG. 4.

In FIGS. 4 and 5, another test tool is illustrated, which can be placed inside a test means casing. The tool 34 has a cylindrical structure 35 around which is placed a plurality of rectangular elements 36 comprising the same type of elements as the circular zones 22 to 28 illustrated in FIG. 2.

Figure 6:
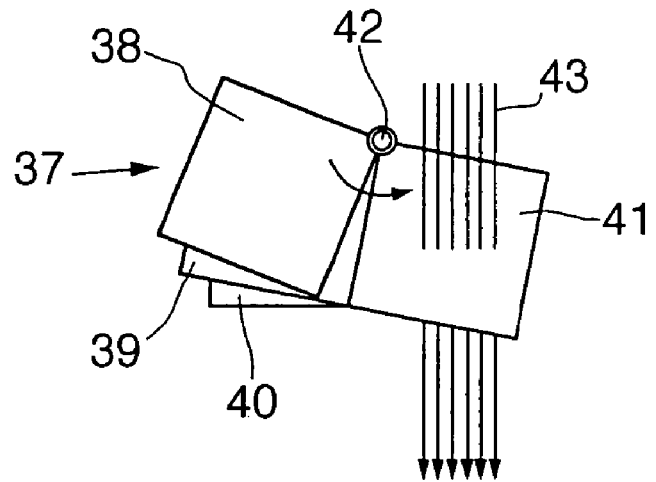

In the embodiment illustrated in FIG. 6, a test tool 37 comprises a plurality of square test elements 38 to 41, each hinged at an angle on an axis 42 ready to be placed on the path of an X-ray beam 43 that is represented here as a beam of parallel lines.

Of course, in both of the foregoing embodiments, the rotation of the tool 34 and of elements 38 to 41 of the tool 37 is motor-driven and monitored by sensor(s) so that the control unit receives information on the position and possibly the movement of these different elements.

Figure 7:
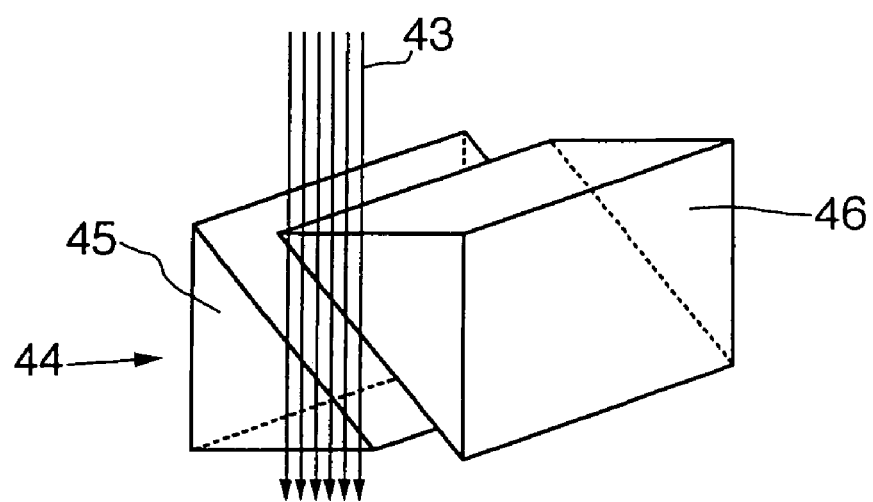

In the embodiment illustrated in FIG. 7, the test tool 44 comprises two blocks 45 and 46 made of a given radiation-absorption material and each having a half-parallelepiped shape cut along a diagonal. The two blocks 45 and 46 complement each other, in the sense that, on bringing them in contact, a rectangular parallelepiped is formed. The X-ray beam 43 crosses the two blocks 45 and 46, the spacing of which determines the thickness of material crossed by the X-ray beam 43. The relative position of the blocks 45 and 46 is detected by sensor and is controlled by means of a motor.

Figure 8:
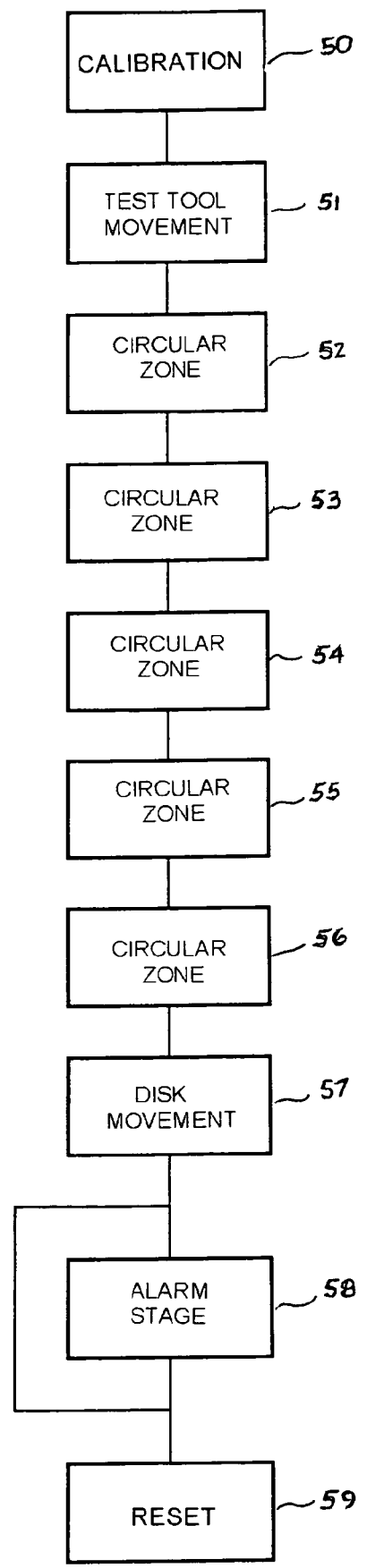
FIG. 8 is a diagram of steps of operation.

Different steps used by a radiology apparatus control unit are illustrated by way of example in FIG. 8 by means of a routine stored in an internal memory of the control unit or outside the control unit.

At step 50, a routine of the control unit, which is dedicated to calibration, verifies the time elapsed since the last calibration and compares it with a predetermined ceiling. If the time elapsed is greater than the ceiling, one then proceeds to step 51; otherwise the program is halted in order to be resumed later, for example, the next day at the same time or after a few minutes of non-use of the radiology apparatus. At step 51, the program controls the movement of a test tool and, by considering the disk 17 of FIG. 2, the positioning of circular zone 23 in place of circular zone 22, which is empty, on the path of the beam 13. Then, a standard calibration is carried out with the circular zone 23. At steps 52 to 56, the program controls the corresponding operations for circular zones 24 to 28.

At stage 57, the routine controls the movement of the disk 17, so that circular zone 22, which is empty, is placed on the path of the beam 13. If, in the course of one of steps 52 to 56, calibration reveals a fault which the control unit cannot remedy by itself, the program controls an alarm stage 58 either on site, for example, on a screen of the radiology apparatus, or at a remote maintenance center, the alarm being advantageously accompanied by a message relating to the nature of the fault, its seriousness, a down time of the radiology apparatus, etc. Otherwise, calibration is terminated and the time elapsed since the last calibration is reset at step 59.

Figure 9:
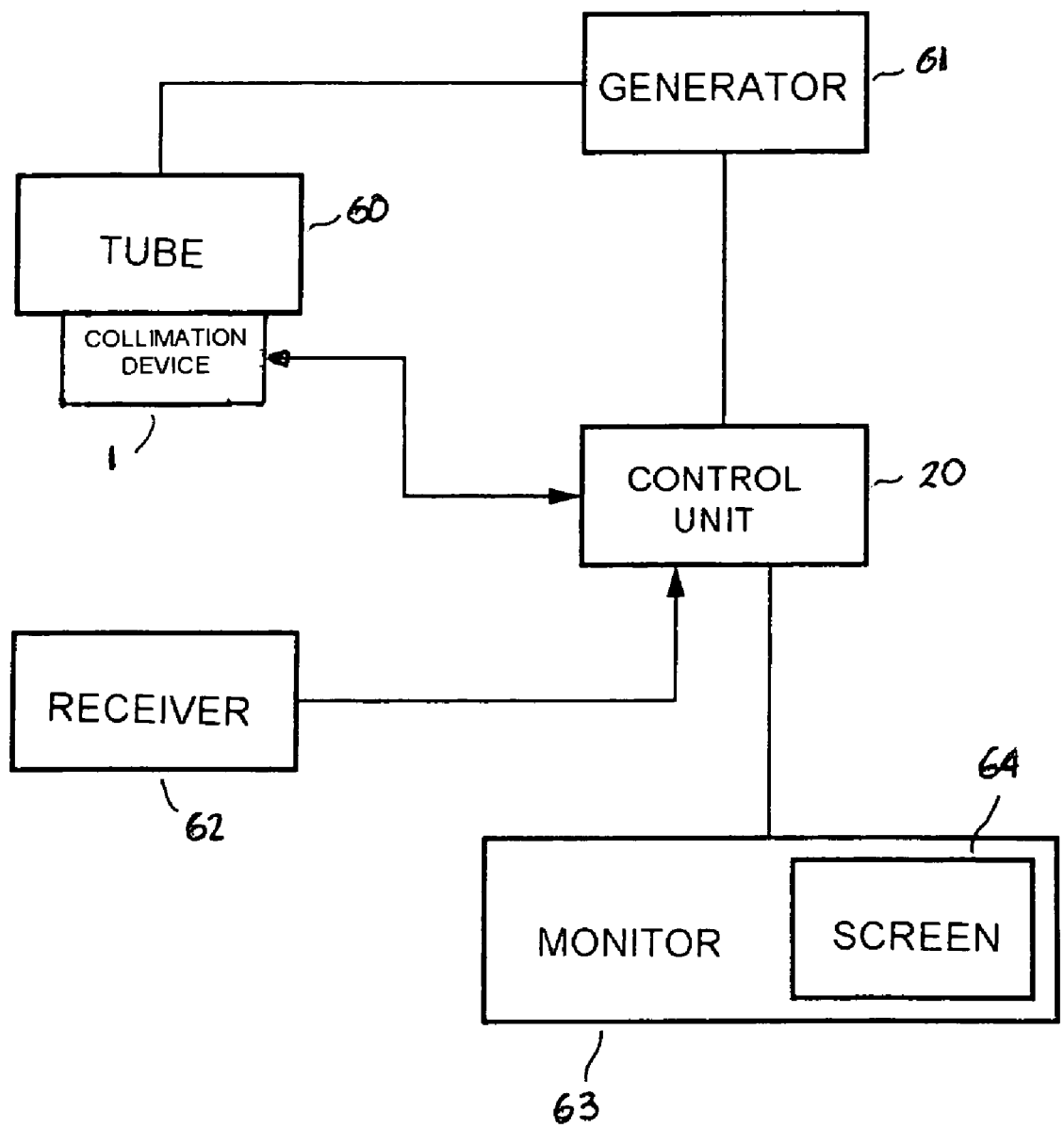
FIG. 9 is a diagram of an architecture of a radiology apparatus.

In FIG. 9, the radiology apparatus comprises, in addition to the central unit 20 and collimation device 1, an X-ray tube 60 integral with the collimation device 1, a high-voltage generator 61 for powering the tube 60, a receiver 62, provided, for example, with a scintillator and a matrix camera, and a monitor 63 provided with a screen 64 for the display of X-ray images.

The present invention makes it possible to design tools for automatic testing of an electromagnetic ray imaging and processing apparatus. The test tools can come in the form of a kit that is added to an existing collimator or can be integrated with a collimator. Remote image quality control can thus be carried out with diagnosis in real time and preventive maintenance. The test tool rests permanently on the imaging apparatus and possesses a deactivated position in which the beam of electromagnetic rays does not encounter any obstacle. The image taken in normal operation of the imaging apparatus does not therefore undergo any attenuation or diminution of quality.

It is important to know precisely the movement of a tool across the beam in order to be able to deduce therefrom an estimate of the remanence and to monitor the progress of remanence in the course of time, that is, aging of the receiver 62 and, notably, of the scintillator. For that purpose, a tool will be moved in a few milliseconds in the X-ray beam intermittently and at constant speed.

The radiology apparatus whose control unit is connected to the test tool is advantageously provided with a remote link, digital, for example, to a maintenance center, which makes it possible to perform a number of maintenance operations without the service call of a maintenance operator.

Other maintenance operations can be carried out with the service call of a maintenance operator, who will have identified the component to be replaced before his trip, which will also make it possible to reduce the number of trips.

The handling of a phantom separate from the apparatus becomes superfluous, which reduces the risks of loss or deterioration of the phantom likely to distort the calibration.

Various modifications in structure and/or steps and/or function may be made by one skilled in the art without departing from the scope and extent of the invention as recited in the claims:

What is claimed is:

1. A method of testing a radiology apparatus an which the apparatus comprises:
    means for emission of an energy beam;
    a collimation device;
    means for receiving the energy beam; and
    means for testing the operation of the radiology apparatus by means of tools forming part of to collimation device, the tools making it possible to functionally define the operation of the means for emission of an energy beam, and the collimation device, the means for testing comprising means including a plurality of test tools with a sensor for sensing the position of each tool.

2. A computer program including program code means for applying the steps of the method according to claim 1.

3. A storage medium which can be read by means for reading program code which are stored therein, the code configured for applying the steps of the method according to claim 1.

4. A generated or stored signal or transmitted or a received signal, the signal embodying a program of instructions executable by a machine to perform the steps of the method according to claim 1.

5. A computer program comprising program code moans wherein the program cods means comprises:
    controlling movement of one or more of a plurality of test tools with a sensor for sensing the position of each tool; and
    positioning one or more of the tools to functionally define operation of emission of an energy beam, a collimation device and means for receiving the energy beam in a radiology apparatus.

6. A computer program product comprising a computer useable medium having computer readable program code means embodied in the medium, the computer program product comprising:
    computer readable program code means embodied in to medium for causing a computer to provide for:
    controlling movement of one or more of a plurality of test tools with a sensor for sensing the position of each tool; and
    positioning one or more of the tools to functionally define operation of emission of an energy beam, a collimation device and means for receiving the energy beam in a radiology apparatus.

7. An article of manufacture for use with a computer system, the article of manufacture comprising a computer readable medium having computer readable program code means embodied in the medium, the program code means comprising:
  computer readable program code means embodied in the medium for causing a computer to provide for:
  controlling movement of one or more of a plurality of test tools with a sensor for sensing the position of each tool; and
  positioning one or more of the tools to functionally define operation of emission of an energy beam, a collimation device and means for receiving the energy beam in a radiology apparatus.

8. A program storage device readable by a machine tangibly embodying a program of instructions executable by the machine, the program of instructions embodied in a medium for causing the machine to provide for:
  controlling movement of one or more of a plurality of test tools with a sensor for sensing the position of each tool; and
  positioning one or more of the tools to functionally define operation of emission of an energy beam, a collimation device and means for receiving the energy beam wherein the machine comprises a radiology apparatus.

9. A wire or wireless communication embodying program of instructions executable by a machine, the program of instructions comprising:
  controlling movement of one or more of a plurality of test tools with a sensor for sensing the position of each tool; and
  positioning one or more of the tools to functionally define operation of emission of an energy beam, a collimation device and means for receiving the energy beam in a radiology apparatus.

* * * * *

UNITED STATES PATENT AND TRADEMARK OFFICE
CERTIFICATE OF CORRECTION

| | |
|---|---|
| PATENT NO. | : 7,021,118 B2 |
| APPLICATION NO. | : 10/867536 |
| DATED | : April 4, 2006 |
| INVENTOR(S) | : Dietmar Sundermann et al. |

Page 1 of 1

It is certified that error appears in the above-identified patent and that said Letters Patent is hereby corrected as shown below:

Column 6,
Line 24, after "apparatus", delete "an" and insert therefor --in--.
Line 30, after "of", delete "to" and insert therefor --the--.
Line 46, after "code", delete "moans" and insert therefor --means--.
Line 47, after "program", delete "cods" and insert therefor --code--.
Line 59, after "in", delete "to" and insert therefor --the--.

Column 8,
Line 8, after "embodying", insert "a".

Signed and Sealed this

Fifteenth Day of August, 2006

JON W. DUDAS
*Director of the United States Patent and Trademark Office*